(12) United States Patent
Oberreither et al.

(10) Patent No.: US 7,998,488 B2
(45) Date of Patent: Aug. 16, 2011

(54) VACCINE FORMULATIONS AND USES THEREOF

(75) Inventors: Manfred Oberreither, Graz (AT); Christa Tauer, Vienna (AT); Falko-Guenter Falkner, Orth/Donau (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 86 days.

(21) Appl. No.: 12/271,522

(22) Filed: Nov. 14, 2008

(65) Prior Publication Data
US 2010/0124557 A1 May 20, 2010

(51) Int. Cl.
*A61K 39/285* (2006.01)
*C12N 7/00* (2006.01)
*C12N 7/01* (2006.01)

(52) U.S. Cl. ............... 424/199.1; 435/235.1; 424/232.1

(58) Field of Classification Search .................. None
See application file for complete search history.

(56) References Cited

U.S. PATENT DOCUMENTS

| | | | | |
|---|---|---|---|---|
| 2,879,202 | A * | 3/1959 | Stewart Aiston et al. | 424/217.1 |
| 3,577,524 | A * | 5/1971 | Pratt | 424/232.1 |
| 4,147,772 | A | 4/1979 | McAleer et al. | |
| 4,824,668 | A | 4/1989 | Melchior et al. | |
| 5,185,146 | A * | 2/1993 | Altenburger | 424/199.1 |
| 5,391,491 | A | 2/1995 | Mundt et al. | |
| 6,960,345 | B2 | 11/2005 | Moyer | |
| 7,256,037 | B2 | 8/2007 | Ellenhorn et al. | |
| 2003/0215455 | A1 | 11/2003 | Reynolds et al. | |
| 2006/0008465 | A1 | 1/2006 | Steinaa et al. | |

FOREIGN PATENT DOCUMENTS

| | | |
|---|---|---|
| FR | 7 773 M | 3/1970 |
| WO | WO-91/09937 | 7/1991 |
| WO | WO-01/66137 | 9/2001 |
| WO | WO-2005/052116 | 6/2005 |

OTHER PUBLICATIONS

Derwent accession No. 1971-45431S (1971).*
GenBank accession No. AY603355, Vaccinia virus strain Acambis 3000 Modified Virus Ankara (MVA), complete genome, May 15, 2004.
Huang et al., "A time-efficient, linear-space local similarity algorithm", *Adv. Appl. Math.*, 12:337-57 (1991).
Maa et al., "Influenza vaccine powder formulation development: spray-freeze-drying and stability evaluation", *J. Pharm. Sci.*, 93:1912-23 (2004).
Reed et al., "A simple method of estimating fifty per cent endpoints", *Am. J. Hyg.*, 27:493-7 (1938).
Zang et al., "Immunogenicity of lyophilized MVA vaccine for HIV-1 in mice model", *Chem. Res. Chinese U.*, 23:329-32 (2007).
International Search Reporting and Written Opinion of the International Searching Authority, European Patent Office, PCT/US2009/064382, dated Feb. 1, 2010.

* cited by examiner

*Primary Examiner* — Mary E Mosher
(74) *Attorney, Agent, or Firm* — Marshall, Gerstein & Borun LLP

(57) ABSTRACT

A liquid or liquid-frozen composition comprising: a modified vaccinia Ankara (MVA) virus or variant or derivative thereof and mannitol, wherein mannitol is the sole stabilization agent of the composition. The mannitol may provide a stabilizing effect at 0 to +10° C. or in a liquid-frozen composition, for example between −10° C. and −30° C. or between −20° C. and −23.5° C. The MVA may be used as a vaccine or for use in gene therapy, virotherapy, immunotherapy, or cancer therapy in a mammal, preferably a human.

18 Claims, 3 Drawing Sheets

VACCINE FORMULATIONS AND USES THEREOF

FIELD OF THE INVENTION

This invention relates to stable formulations of viruses and virus-based vaccines. A difficulty in stabilizing viruses at temperatures below the freezing point of water is preventing the physical disruption of structural and functional components during freezing and thawing. In order to ensure stability during storage, stocks of infective virus have commonly been stored at $\leq -60°$ C. In addition, chilled (e.g. 5-8° C.) preparations of viruses can have limited stability.

GENERAL BACKGROUND OF THE INVENTION

Modified vaccinia Ankara (MVA) is a highly attenuated member of the genus Orthopoxvirus in the family of Poxviridae. Poxviruses engineered to express foreign genes are established tools for target protein synthesis and vaccine development in biomedical research. Their favorable characteristics include a large packaging capacity for recombinant DNA, precise virus-specific control of target gene expression, lack of persistence or genomic integration in the host, high immunogenicity as vaccine, and ease of vector and vaccine production.

MVA arose as an alternative to vaccinia virus (VV) smallpox vaccine after safety concerns instigated the development of viruses that are replication-defective in human cells. After more than 570 passages in chicken embryo fibroblasts MVA had lost the broad cellular host range of VV, being unable to effectively grow in many cells of mammalian origin, including human cells. MVA has been used for the primary smallpox vaccination of more than 100,000 people without serious problems and was considered avirulent after testing in laboratory animals.

For most purposes the generation of MVA vectors requires a single genomic insertion from a plasmid that carries one or two recombinant genes being placed under control of a VV-specific promoter. The sites of naturally occurring deletions within the MVA genome or the gene loci encoding the VV proteins thymidine kinase or hemagglutinin serve as sites for the insertion of recombinant gene sequences.

Much previous research has been dedicated to the development of MVA candidate recombinant vaccines against multiple virus infections of humans, including those causing AIDS, influenza, early childhood respiratory diseases, measles, Japanese encephalitis, dengue fever or malaria. As an effective vaccine against AIDS is urgently needed, recombinant MVA producing immunodeficiency virus antigens are among the first vector viruses to be evaluated as candidate vaccines in humans.

Viruses are often unstable outside their native environments, which can vary considerably among cell compartments and extracellular fluids. If certain conditions are not maintained, purified viruses may not function properly or remain soluble. Furthermore, virus titer can be affected by proteolysis, aggregation and suboptimal buffer conditions. Purified viruses for use in vaccination, for example, often need to be stored for extended periods of time while retaining their original structural integrity and/or activity. The extent of storage 'shelf life' can vary from a few weeks to more than a year and is dependent on the nature of the virus and the storage conditions used.

To ensure stability, therapeutic viral formulations are generally supplied either as lyophilized material to be dissolved just before use in a separately packaged water soluble diluent; however, this process increases manufacturing costs, and involves an increased risk of improper administration as the lyophilized protein needs to be dissolved just prior to use and, usually, a loss in infectivity titer is seen after the lyophilization process. Alternatively, therapeutic viral formulations may be supplied as solutions containing additives for improving stability. For example, additives such as free amino acids (e.g., leucine, tryptophan, serine, arginine and histidine) useful in formulating protein solutions have been proposed. Some viral formulations currently available on the market contain a protein as a stabilizer. Human serum albumin (HSA) or purified gelatin can be used to suppress chemical and physical changes in viral solutions. However, the addition of these proteins involves a complicated process for removing viral contamination. Furthermore, they can produce strong anaphylactic responses which limits their use.

Liquid viral formulations are commonly stored as frozen solids. Conventional cryopreservation utilizes a range of additives to promote vitrification. Vitrification is a process of converting a material into a glass-like amorphous solid which is free from any crystalline structure, either by the quick removal or addition of heat, or by mixing with an additive. Solidification of a vitreous solid occurs at the glass transition temperature (which is lower than the melting temperature, $T_m$, due to supercooling). Additives used in cryobiology or produced naturally by organisms living in polar regions are called cryoprotectants. Conventional cryoprotection focuses on achieving a solid state which is most favorable for the long-term storage of biological materials, i.e., on the transition from a liquid to a solid state.

However, it is the surprising finding of this study that once a solid frozen state is achieved, viral compositions may be unstable.

SUMMARY OF THE INVENTION

A first aspect of the invention provides a liquid or liquid-frozen composition comprising:
  (a) a modified vaccinia Ankara (MVA) virus or variant or derivative thereof; and
  (b) mannitol,
wherein (b) is the sole stabilization agent of the composition
The compositions of the invention are stable.

Mannitol is frequently used in lyophilized viral vaccine formulations as a bulking or caking agent. For example, Maa et al., (2004, *J. Pharm. Sci* 93(7):1912-1923) discloses influenza vaccine spray-freeze-dried formulations comprising mannitol, dextran and inositol. The authors primarily used mannitol as a hygroscopicity agent but also hypothesized that vaccine stability was improved by enhancement of the mechanical strength of dehydrated particles.

Use of mannitol as a stabilizer in lyophilized MVA-based vaccines is known in the art. Zang et al., (2007, *Chem. Res. Chinese U.*, 23(3):329-332) described stable lyophilized MVA vaccine compositions comprising trehalose, mannitol, dextran and inositol. Trehalose and dextran were reported to promote native protein structure preservation whereas mannitol and inositol were said to act as free-radical oxidation inhibitors.

Mannitol has also used in liquid vaccine formulations, including MVA-based vaccines. U.S. application Ser. No. 11/202,516 listed mannitol in its general disclosure as a possible excipient in combination with trehalose and/or dextran. However, no desired property of mannitol was described. Similarly, U.S. application Ser. No. 10/379,572 disclosed oral MVA-smallpox vaccine formulations optionally comprising mannitol together with other excipients including AFFA (a nutritional grade fish oil), Hetastarch, and glycerol. Again, no desirable functional property of mannitol was described. U.S. Pat. No. 7,256,037 described MVA liquid formulations optionally containing mannitol as an isotonicity agent.

The use of mannitol as a stabilization agent in liquid and liquid-frozen viral vaccine compositions has also been reported. Mannitol was cited as a viral stabilizer by virtue of being both a cryoprotectant and free-radical scavenger in WO 2001/066137 and WO 2005/052116. WO 2001/066137 also stated that the virus of the composition(s) may optionally be a vaccinia virus. Furthermore, U.S. Pat. No. 4,147,772 also cited mannitol as a stabilizer of liquid vaccine formulations. However, none of these disclosures utilized mannitol as a sole stabilization agent. Rather, stability was achieved using a combination of excipients that may have comprised mannitol.

By "variant" we mean that the viral genome does not share 100% nucleic acid sequence identity with that of modified vaccinia Ankara (MVA) (GenBank accession number AY603355, VRL 15 May 2004) but is still able to confer immunity to smallpox and to infect chicken embryo fibroblasts, whilst being unable to replicate in the human HeLa cell line. For example, the genome may comprise a nucleic acid sequence with at least 90% identity to the nucleic acid sequence of MVA, more preferably at least 91%, 92%, 93%, 94%, 95%, 96%, 97%, 98% or 99% identity to said nucleic sequence.

Percent identity can be determined by methods well known in the art, for example using the LALIGN program (Huang and Miller, *Adv. Appl. Math.* (1991) 12:337-357) at the Expasy facility site using as parameters the global alignment option, scoring matrix BLOSUM62, opening gap penalty −14, extending gap penalty −4.

By "derivative" we mean recombinant MVAs comprising genomic insertions, deletions and/or substitutions.

By "stable" we mean that the virus titer of the composition after 4 weeks of storage, at 8° C.±2° C. or −23° C.±5° C. is at least 20% of its original virus titer prior to storage, more preferably at least 30% or 40% or 50% or 60% 70% or 80% or 85% or 90% of original infectivity, and most preferably at least 95%, 96%, 97%, 98% or 99% of original virus titer. Preferably the virus titer of the composition maintained at this/these level(s) after at least 3 months of storage and preferably after 6 months, 1 year, 2 years, 3 years or 4 years of storage and most preferably after 5 or more years of storage.

By "stabilization agent" we mean an agent that promotes the maintenance of virus titer as compared with an equivalent composition lacking the agent. Typically, instability can be detected in comparative studies within 1 month to several months of frozen storage. However the stabilizing effect provided by the agent of the invention may extend through the full lifetime of the composition which may be 5 years or more. Preferably the composition comprising the stabilization agent will have at least 20% greater virus titer than an equivalent composition lacking the stabilization agent after 4 weeks of storage, at 8° C.±2° C. or −23° C.±5° C. more preferably at least 30% or 40% or 50% 60% or 70% or 80% or 85% or 90% greater virus titer. Preferably the virus titer of the composition comprising the stabilization agent is maintained at this/these level(s) compared to an equivalent composition lacking the stabilization agent after at least 3 months of storage and preferably after 6 months, 1 year, 2 years, 3 years or 4 years of storage and most preferably after 5 or more years of storage. By "stabilization agent" we do not include typical pharmaceutical composition excipients such as (but not limited to) preservatives, buffering agents, antimicrobial agents, bulking/extender agents, viscosity agents, isotonicity agents, detergents, emulsifiers and surfactants.

Conversely, by "stabilization agent" we do include simple sugars such as sucrose, dextrose, glucose and fructose; sugar alcohols/polyols such as glycerol, sorbitol, xylitol, erythritol and inositol; and serum albumins such as human serum albumin (HSA) or bovine serum albumin (BSA)

Virus titer can be measured using any standard technique known in the art such as plaque assays (where appropriate) or $TCID_{50}$ assays and so on. In viral plaque assays, visible structures are formed in a cell culture contained within some nutrient medium. By propagating within the cell cultures, the viruses generate zones of cell destruction known as plaques. These plaques can be detected visually, sometimes with the naked eye, and sometimes through other techniques such as staining, microscopy, hemadsorption or immunofluorescence, to determine virus titer.

$TCID_{50}$ (tissue culture infective dose 50) assays determine the quantity of an infectious agent, for example a virus, that when inoculated onto a number of susceptible tissue cultures will infect 50% of the individual cultures.

To determine $TCID_{50}$, Chicken embryo cells (CECs) are prepared, for instance, according to the methods of U.S. Pat. No. 5,391,491 (with or without serum) essentially as described below. Microtiter plates are seeded with 100 μl of CEC suspension at a concentration of $5\times10^5$±20% cells/ml. The plates are incubated overnight at 36° C.±2° C. in a $CO_2$-incubator.

Samples and control preparation (controls) are treated with ultrasound prior to dilution. Samples and controls are diluted in tenfold steps in cell culture medium to generate a dilution series covering integer log or half-logarithmic steps. The appropriate number of dilution steps depends on the expected virus titer. Recombinant MVA placebo samples are tested starting with undiluted sample.

100 μl of each prepared sample- or controls-dilution, respectively, is transferred eight times to the prepared microtiter plates, containing a CEC monolayer. An additional eight wells are inoculated with cell culture medium as negative (cell) control. The microtiter plates are subsequently incubated for 5±1 days at 36±2° C. in a $CO_2$-incubator.

The wells of the microtiter plates are screened under a reverse light microscope for local lesions (Cytopathic effect (CPE) caused by MVA) in the cell layer. From the percentage of wells showing CPE at each dilution, the $TCID_{50}$ is calculated.

The assay is considered as valid if the cell control is free of CPE and the virus titer of the positive control is in the range of the desired value. The statistical calculation of the $TCID_{50}$ is performed according to known algorithms (e.g. Reed & Muench, 1938, *Am. J. Hyg.,* 27:493-497) by means of an appropriate computer program. Calculation of double or multiple determinations of one sample are typically performed individually. Arithmetic mean of all valid individual results are calculated using following formula:

$$\overline{X} = \frac{1}{n} * \sum_{i=1}^{n} X_i$$

X=arithmetic mean, virus-titer of the sample [$TCID_{50}$/ml]

$X_i$=valid individual results, virus-titer of the sample [$TCID_{50}$/ml]

n=number of individual determinations

Conventional freezers or cold rooms, used for long-term storage of frozen foods, are commonly also used for storage of live vaccines. They are designed to operate at ≦−15° C. but frequently reach temperatures between −18° C. and −26° C.

Vaccine compositions may also be stored below conventional freezer temperatures, for example at −80° C. (in industrial freezers for long-term storage of biological materials) or −160° C. (in liquid nitrogen). It may also be preferable to store vaccines at conventional refrigeration temperatures (e.g., 2° C. to 8° C.) or at ambient temperature.

Frozen storage of vaccines is both expensive and environmentally damaging due to increased electrical consumption and production/release of chemicals for refrigeration. Particularly in regions with a hot climate, and especially in cases where the maintenance of a cold storage line from the manufacturing laboratory to the places of utilization is required, refrigeration may prove to be insufficient or may be interrupted. It is therefore preferable to provide a stable and heat-resistant vaccine, capable of withstanding deterioration when it is exposed accidentally to high temperatures. Even by complying with extremely drastic restrictions of storage and shipment, it is not always possible to avoid vaccines being exposed, in the course of their storage and their shipment, to high temperatures. This can cause loss of virus titer of these vaccines and, hence, loss of their activity. Thus, it is desirable to provide additives that also improve virus stability at hyper-refrigeration temperatures.

Preferably mannitol provides a stabilizing effect for the virus of the composition when the composition is in a solid state, for example, when the composition is below freezing temperature (i.e., a liquid-frozen composition). It is also preferable that mannitol provides a stabilizing effect when the composition is not in a solid state, for example, when the composition is above freezing temperature (i.e., a liquid composition). Preferably the mannitol of the composition may provide a stabilizing effect at storage temperatures between 10° C. and 0° C., for example between 8° C. and 2° C., between 6.5° C. and 3.5° C. or between 5° C. and 3° C.

Mannitol may provide a stabilizing effect in a recrystallization window of the composition. The term "recrystallization window" refers to the temperature range in which, at a given pressure, one crystal structure (for example, in ice or a clathrate hydrate) is capable of transitioning to a different crystal structure, from an amorphous structure to a crystal structure or from a crystal structure to an amorphous one. This physical transition produces mechanical stresses, such as compression or shearing, on materials suspended or otherwise contained in the frozen liquid. An important factor in protecting viruses from inactivation at moderately low temperatures (e.g., $\leq$−15° C. and $\geq$−28° C.) is preventing the denaturation or rupture of the structure and functional components during freezing and storage.

The term, "recrystallization" relates to phase transitions of solid state liquids such as ice. Everyday ice and snow has a hexagonal crystal structure (ice $I_h$). Subjected to varying temperatures and/or pressures ice can form in more than a dozen different phases. These include II, III, V, VI, VII, VIII, IX, and X; each of which can be formed at ambient pressure. The different types of ice are differentiated by their crystalline structure, ordering and density. There are also two metastable phases of ice under pressure, both fully hydrogen disordered, namely IV and XII.

As well as crystalline forms, solid water can exist in amorphous states as amorphous solid water (ASW). Amorphous ice is an ice lacking crystal structure and exists in at least three forms: low-density (LDA) formed at atmospheric pressure or below, high density (HDA) and very high density amorphous ice (VHDA), forming at higher pressures. LDA forms by extremely quick cooling of liquid water ("hyperquenched glassy water", HGW), by depositing water vapor on very cold substrates ("amorphous solid water", ASW) or by heating high density forms of ice at ambient pressure ("LDA"). However, the presence of multiple solutes in viral compositions means that crystal forms and phase transitions not seen in pure ice are possible.

The recrystallization window of the present compositions may be, for example, between −10° C. and −30° C. or between −20° C. and −23.5° C.

A recrystallization window may be determined using differential thermal analysis (DTA) or differential scanning calorimetry (DSC) etc.

Thermal analysis comprises a group of techniques in which a physical property of a substance is measured as a function of temperature, while the substance is subjected to a controlled temperature program. In differential thermal analysis, the temperature difference that develops between a sample and an inert reference material is measured, when both are subjected to identical heat treatments. The related technique of differential scanning calorimetry relies on differences in energy required to maintain the sample and reference at an identical temperature. Length or volume changes that occur on subjecting materials to heat treatment are detected in dilatometry; X-ray or neutron diffraction can also be used to measure dimensional changes. Both thermogravimetry and evolved gas analysis are techniques that rely on samples which decompose at elevated temperatures. The former monitors changes in the mass of the specimen on heating, whereas the latter is based on the gases evolved on heating the sample. Data from these techniques can be related to changes in the defect density of materials or to study phase transitions (such as crystallization or recrystallization).

For example, crystallization and other phase transitions may be determined using a DCS Q1000 Differential Scanning Calorimeter (available from TA Instruments, New Castle, Del., USA) according to the manufacturer's instructions.

The composition may be a vaccine or may be for use in gene therapy, virotherapy, immunotherapeutics, or cancer therapy. Preferably the composition is a live vaccine. The composition may be for vaccination of a mammal, preferably a human.

Gene therapy is the insertion of genes into an individual's cells and tissues to treat a disease, and hereditary diseases in which a defective mutant allele is replaced with a functional one. Although the technology is still in its infancy, it has been used with some success. Antisense therapy is not strictly a form of gene therapy, but is a genetically-mediated therapy and is often considered together with other methods.

Virotherapy is a form of cancer treatment using viruses modified to target attack cancerous cells while leaving healthy cells undamaged. Immunotherapeutics is passive immunization of an individual by administration of pre-formed antibodies (serum or gamma globulin) actively produced in another individual; by extension, the term has come to include the use of immunopotentiators, replacement of immunocompetent lymphoid tissue (e.g., bone marrow or thymus), etc.

The virus may be for vaccination against a disease or condition caused by a virus in a viral family selected from Adenoviridae, Flaviviridae, Herpesviridae, Herpadnaviridae, Orthomyxoviridae, Papovaviridae, Paramyxoviridae, Picornaviridae, Poxviridae, Reoviridae, Retroviridae, Rhabdoviridae and Togaviridae. The virus may be for vaccination against a disease or condition caused by adenovirus, herpes simplex, varicella zoster, cytomegalovirus, Epstein Barr virus, hepatitis B virus, influenza virus, human papilloma viruses, parainfluenza virus, measles virus, respiratory syncytial virus, poliovirus, Coxsackie virus, rhinovirus, hepatitis A virus, vaccinia, variola, rotavirus, human T lymphotropic virus-1, human immunodeficiency virus (HIV), rabies virus, rubella virus, arbovirus or by intracellular pathogens/parasites including *Afipia* spp, *Brucella* spp, *Burkholderia pseudomallei*, *Chlamydia*, *Coxiella burnetii*, *Francisella tularensis*, *Legionella pneumophila*, *Listeria monocytogenes*, *Mycobacterium avium*, *Mycobacterium leprae*, *Mycobacterium tuberculosis*, *Neisseria gonorrhoeae*, *Rickettsiae*, *Salmonella typhi*, *Shigella dysenteriae*, *Yersinia pestis*, *Plasmodium* spp, *Theileria parva*, *Toxoplasma gondii*, *Cryptosporidium parvum*, *Leishmania*, *Trypanosoma cruzi* and *Cryptococcus neoformans*.

In particular the virus may be for vaccination against smallpox or Yellow fever.

Alternatively the virus may be for immunotherapy (induction of an immune response by a tumor-associated antigen (TAA) expressed by a recombinant virus), cancer therapy (see above, including oncolytic therapy by live viruses with tumor tropism) or treatment of virus-associated malignancies.

The virus may be a non-enveloped virus or an enveloped virus. The virus may be a poxvirus, for example, a modified vaccinia Ankara (MVA) virus. Preferably the virus is a recombinant modified vaccinia Ankara virus.

The virus may be a non-recombinant MVA used for vaccination against smallpox.

The virus may be a recombinant MVA pox virus that delivers the gene encoding a tumor-associated antigen. Such modified viruses are used in cancer therapy to induce an immune response.

The composition may comprise one or more preservatives, buffering agents, isotonicity agents or other conventional components used in formulating pharmaceutical compositions, for example Tween® polysorbates, polyethylene glycol, calcium chloride, lecithins such as phosphatidyl choline, phosphate, vitamin A, vitamin E, vitamin C, retinyl palmitate, selenium, methionine, citric acid, sodium citrate, or synthetic preservatives like methyl paraben and propyl paraben. The composition may be pH buffered, for example with Tris buffered saline (TBS) or phosphate buffered saline (PBS).

The pH of the composition may be between 6 and 9, for example between 6.5 and 8.5, 7 and 8.5, 7.5 and 8.5 or 8 and 8.5. The pH of the composition may be 8.2.

The composition is preferably substantially free of human serum albumin and preferably substantially free of any serum albumin. The composition is also preferably substantially free of non-viral protein.

By "substantially free of human serum albumin" we mean that the composition comprises 0.1% (w/v) human serum albumin, or less. For example, the composition may comprise 0.01%, 0.001%, 0.0001% or 0.00001% (w/v) human serum albumin. Preferably, there is no human serum albumin present.

By "substantially free of non-viral protein" we mean that the composition comprises 0.1% (w/v) non-viral protein, or less. For example, the composition may comprise 0.01%, 0.001%, 0.0001% or 0.00001% (w/v) non-viral protein. Preferably, there is no non-viral protein present.

The composition preferably comprises between 0.01% and 40% (w/v) mannitol, for example, between 0.1% and 10%, 1% and 20%, 1% and 10%, 2% and 9%, 3% and 8% or between 4% and 6%. Most preferably the composition comprises about 5% (w/v) mannitol. The composition may also comprise 20 mM Tris, 135 mM NaCl and it may be adjusted to pH 8.2 using HCl.

Compositions in accordance with the present invention that are suitable for oral administration may be presented as discrete units, such as capsules or cachets, each containing a predetermined amount of the composition; as a solution in an aqueous liquid or a non-aqueous liquid; or as an oil-in-water liquid emulsion or a water-in-oil liquid emulsion. The composition may also be presented as a bolus, electuary or paste.

Preferably, compositions of the invention are suitable for parenteral administration including aqueous and non-aqueous sterile, non-pyrogenic injection solutions which may contain buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials. In one embodiment, the composition is substantially aqueous.

It should be understood that in addition to the ingredients particularly mentioned above the formulations of this invention may include other agents conventional in the art having regard to the type of composition in question, for example those suitable for oral administration may include flavoring agents.

A second aspect of the invention provides method of stabilizing a liquid or liquid-frozen composition comprising a modified vaccinia Ankara (MVA) or variant or derivative thereof, the method comprising adding a sufficient amount of mannitol, wherein mannitol is the sole stabilization agent of the composition.

The agent may provide a stabilizing effect as defined above and the composition may be for a purpose as defined above. The virus of the composition may be as defined above and the composition itself may be as defined above.

A third aspect of the invention provides the use of mannitol to stabilize liquid or liquid-frozen composition comprising a modified vaccinia Ankara (MVA) or variant or derivative thereof wherein mannitol is the sole stabilization agent of the composition.

The agent may provide a stabilizing effect as defined above and the composition may be for a purpose as defined above. The virus of the composition may be as defined above and the composition itself may be as defined above.

Exemplary aspects of the invention are described in the following non-limiting examples, with reference to the above figures.

EXAMPLES

Example A

Frozen Liquid Vaccine Formulations are Unstable at Conventional Storage Temperatures. Addition of Mannitol Confers Stability to Vaccine Formulations at Conventional Storage Temperatures Introduction This study was conducted with recombinant MVA and MVA as test articles. The recombinant MVA is a gene-based, anti-cancer immunotherapeutic. The Modified Vaccinia Ankara (MVA) Smallpox Vaccine is a live, attenuated vaccine for the prevention and control of smallpox. The purpose of this study was to test the stability of liquid formulations stored under conventional refrigeration conditions.

Material and Methods

Formulation

Large scale production of MVA was achieved in a serum-free modification of the methods described in U.S. Pat. No. 5,391,491. Formulation was done by dilution of batch MVA by dilution in TBS to a target titer of 1×10$^9$ TCID$_{50}$/ml.

Storage Characterization

Formulations were stored at:

−23° C.±2° C.;   (i)

<−60° C.   (ii)

Determination of TCID$_{50}$

Microtiter plates were seeded with 100 µl of CEC suspension at a concentration of 5×10$^5$±20% cells/ml. The plates were incubated overnight at 36±2° C. in a CO$_2$ incubator.

Samples and control preparation (controls) were treated with ultrasound prior to dilution. Samples and control were diluted in tenfold steps in cell culture medium to generate a dilution series covering integer log or half-logarithmic steps. The appropriate number of dilution steps depended on the expected virus-titer.

100 µl of each prepared sample- or control-dilution, respectively, was transferred eight times to the prepared microtiter plates, containing a CEC monolayer. An additional eight wells were inoculated with cell culture medium as negative (cell) control. The microtiter plates were subsequently incubated for 5±1 days at 36±2° C. in a CO$_2$ incubator.

The wells of the microtiter plates were screened under a reverse light microscope for local lesions (Cytopathic effect (CPE) caused by MVA) in the cell layer. From the percentage of wells showing CPE at each dilution, the TCID$_{50}$ was calculated.

The assay was considered as valid if the cell control was free of CPE and the virus titer of the positive control was in the range of the desired value. The statistical calculation of the TCID$_{50}$ was performed according to known algorithms (e.g. Reed & Muench, 1938, *Am. J. Hyg.*, 27:493-497) by means of an appropriate computer program.

The control sample is a standard MVA preparation, in TBS (stored in hundreds of aliquots frozen at less than −60° C.) that has been titrated several time (10-20 times or more). The repeated titration results in a stable average titer value that can be used as a titration standard.

Results

Figure 1:
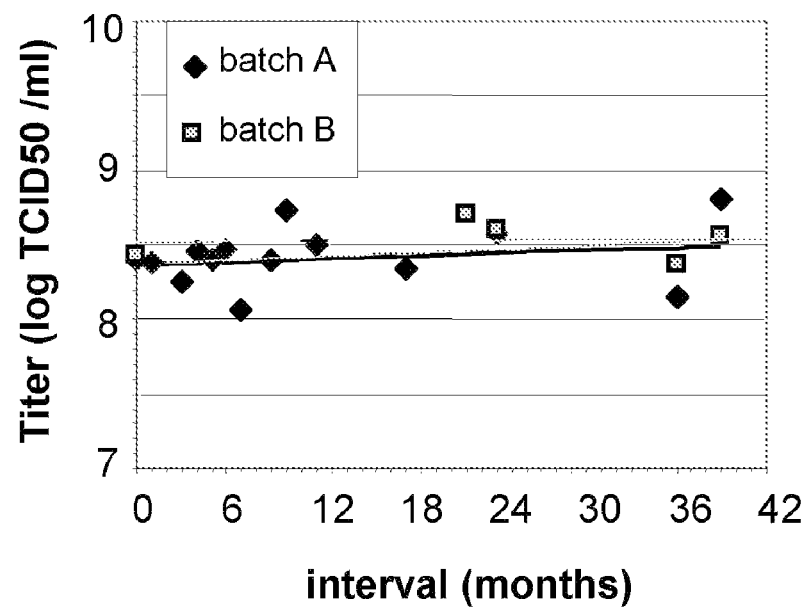
FIG. 1—$TCID_{50}$ values of MVA TBS (liquid-frozen) compositions between −60° C. and −80° C. Two MVA TBS compositions (batches A and B) were stored at −60° C. (±5° C.) for a 39 month period. Samples were taken at intervals and $TCID_{50}$ values determined. The formulations were stable over the course of the trial.

MVA compositions in Tris-Buffered Saline (TBS) were found to be stable at less than −60° C. for a 39 month period (see FIG. 1). There was the general belief that a liquid frozen formulation stored under normal freezing conditions (i.e. around −20° C.) would also be stable. Thus, it was expected that the same MVA TBS formulations would be stable at normal freezing temperatures.

Figure 2:
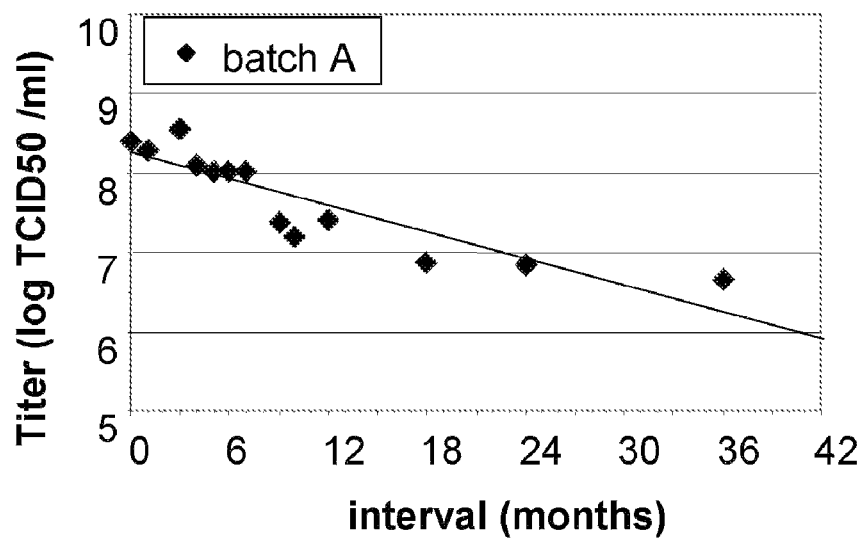
FIG. 2—$TCID_{50}$ values of MVA TBS (liquid-frozen) compositions at −23° C. (±2° C.). A MVA TBS composition (batch A) was stored at −23° C. (±2° C.) for a period of 36 months. Samples were taken at intervals and $TCID_{50}$ values determined. The composition was unstable over the course of the trial.
Figure 5:
FIG. 5—TCID$_{50}$ values of recombinant MVA TBS-mannitol (liquid) compositions at −23° C. Five recombinant MVA TBS-mannitol (5% w/v) compositions (batches D to H) were stored at −23° C. for an 18 month period. Samples were taken at intervals and TCID$_{50}$ values determined. Each of the formulations was stable over the course of the trial.

However, as shown in FIG. 2, MVA TBS formulations were, over a 36 month period, surprisingly found to be unstable at −23° C. Addition of 5% mannitol was sufficient to stabilize the virus of such compositions (see FIG. 5).

Discussion

Liquid MVA TBS formulations were found to be unstable between temperatures of −22° C. to −23.4° C. The reason for this instability may be a recrystallization of the aqueous phase occurring in this temperature range of this formulation. The formulation was stabilized in this temperature range by the addition of 5% (w/v) mannitol. Hence, liquid MVA TBS-mannitol formulations are stable at typical storage temperatures of −23° C.±2° C.

Example B

A Liquid TBS Vaccine Formulation was Unstable at +2° C. to +8° C. whereas TBS-Mannitol Vaccine Formulations are Stable at these Temperatures Introduction The objective of this liquid formulation study was to determine whether the addition of mannitol to a Tris buffered saline (TBS) vaccine formulation impacted upon its stability during refrigerated (non-frozen) storage.

Material and Methods

Formulation

Large scale production of MVA was achieved in a serum-free modification of the methods described in U.S. Pat. No. 5,391,491. Formulation was done by dilution of batch MVA by dilution in TBS to a target titer of 1×10$^9$ TCID$_{50}$/ml. Mannitol was added to a final concentration of 5%.

Storage Conditions

5° C.±3° C.   (i)

Determination of TCID$_{50}$

As for Example A (above).

Results

Storage Stability

Figure 3:
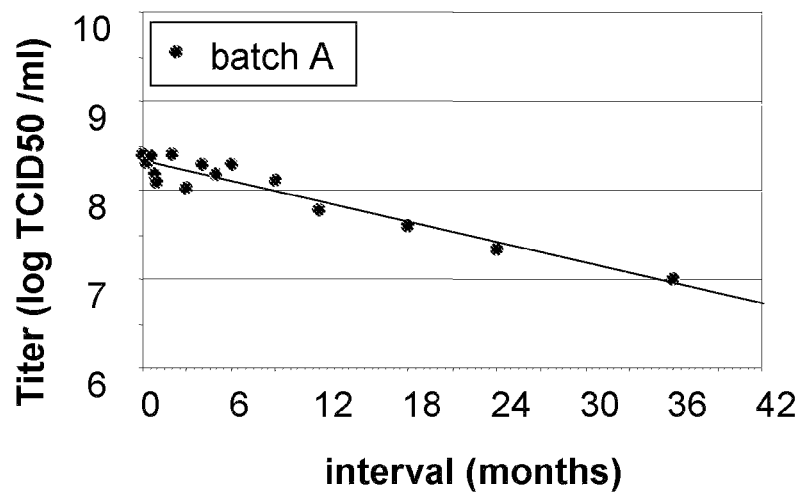
FIG. 3—$TCID_{50}$ values of MVA TBS (liquid) compositions at +2° C. to +8° C. A MVA TBS composition (batch A) was stored at +2° C. to +8° C. for a 36 month period. Samples were taken at intervals and $TCID_{50}$ values determined. The formulation was unstable over the course of the trial.
Figure 4:
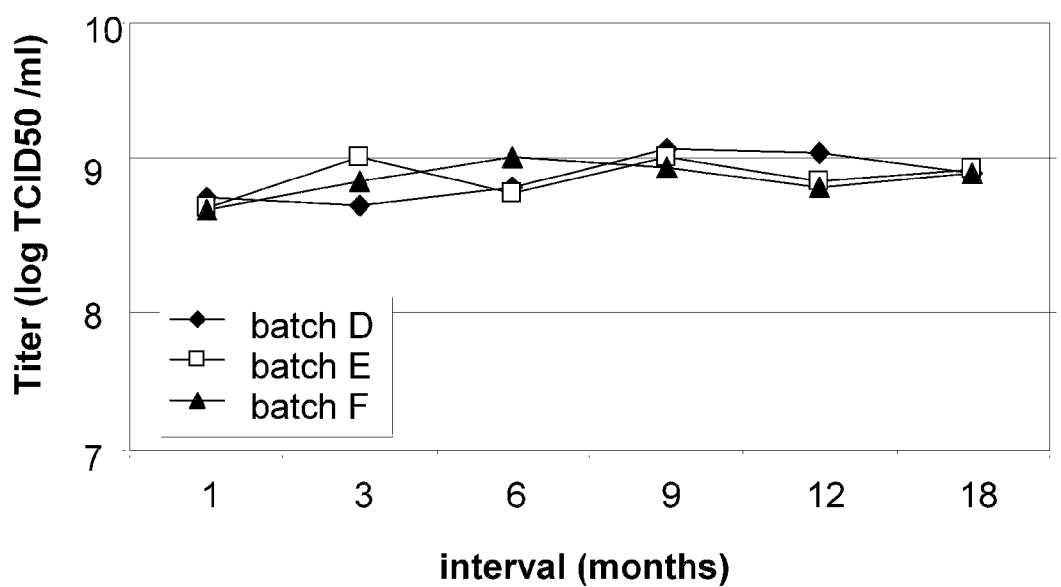
FIG. 4—$TCID_{50}$ values of recombinant MVA TBS-mannitol (liquid) compositions at +2° C. to +8° C. Three recombinant MVA TBS-mannitol (5% w/v) compositions (batches D, E and F) were stored at +2° C. to +8° C. for a 12 month period. Samples were taken at intervals and $TCID_{50}$ values determined. Both formulations were stable over the course of the trial.

An MVA TBS composition was found to be unstable when stored at 2° C. to 8° C. over a period of 12 to 36 months (see FIG. 3). However, three MVA TBS compositions containing 5% w/v mannitol were found to be stable over the course of an 18 month trial (see FIG. 4).

Discussion

These data suggest that while liquid TBS vaccine formulations were unstable at refrigeration temperatures (+2° C. to +8° C.), the addition of 5% mannitol provided a stabilizing effect.

The invention claimed is:

1. A liquid or liquid-frozen composition comprising:
   (a) a modified vaccinia Ankara (MVA) virus or variant thereof; and
   (b) mannitol,
   wherein (b) is the sole stabilization agent of the composition, and wherein the composition is substantially free of non-viral protein.

2. The composition according to claim 1 wherein mannitol provides a stabilizing effect at storage temperatures between 10° C. and 0° C.

3. The composition according to claim 1 wherein the virus is live.

4. The composition according to claim 3 wherein the MVA is a recombinant vector virus comprising an immunogenic or therapeutic gene sequence.

5. The composition according to claim 4 wherein the immunogenic gene sequence is from a microorganism selected from the group consisting of adenovirus, herpes simplex, varicella zoster, cytomegalovirus, Epstein Barr virus, hepatitis B virus, influenza virus, human papilloma viruses, parainfluenza virus, measles virus, respiratory syncytial virus, poliovirus, Coxsackie virus, rhinovirus, hepatitis A virus, vaccinia, variola major, variola minor, rotavirus, human T lymphotropic virus-1, human immunodeficiency virus (HIV), rabies virus, rubella virus, Yellow fever virus, arbovirus, *Afipia* spp, *Brucella* spp, *Burkholderia pseudomallei, Chlamydia, Coxiella burnetii, Francisella tularensis, Legionella pneumophila, Listeria monocytogenes, Mycobacterium avium, Mycobacterium leprae, Mycobacterium tuberculosis, Neisseria gonorrhoeae, Rickettsiae, Salmonella typhi, Shigella dysenteriae, Yersinia pestis, Plasmodium* spp, *Theileria parva, Toxoplasma gondii, Cryptosporidium parvum, Leishmania, Trypanosoma cruzi* and *Cryptococcus neoformans*.

6. The composition according to claim 1 wherein the composition is substantially aqueous.

7. The composition according to claim 1 comprising between 0.01% and 40% (w/v) mannitol.

8. The composition according to claim 7 comprising between 0.1% and 10% (w/v) mannitol.

9. The composition according claim 8 comprising about 5% (w/v) mannitol.

10. A method of stabilizing a liquid or liquid-frozen composition comprising a Modified Vaccinia Virus (MVA) or variant thereof, the method comprising adding a sufficient amount of mannitol to the composition, wherein mannitol is the sole stabilization agent of the composition, and wherein the composition is substantially free of non-viral protein.

11. The method according to claim 10 wherein the virus is live.

12. The method according to claim 11 wherein the MVA is a recombinant vector virus comprising an immunogenic or therapeutic gene sequence.

13. The method according to claim 12 wherein the immunogenic gene sequence is from a microorganism selected from the group consisting of adenovirus, herpes simplex, varicella zoster, cytomegalovirus, Epstein Barr virus, hepatitis B virus, influenza virus, human papilloma viruses, parainfluenza virus, measles virus, respirator syncytial virus, poliovirus, Coxsackie virus, rhinovirus, hepatitis A virus, vaccinia, variola major, variola minor, rotavirus, human T lymphotropic virus-1, human immunodeficiency virus (HIV), rabies virus, rubella virus, Yellow fever virus, arbovirus, *Afipia* spp, *Brucella* spp, *Burkholderia pseudomallei, Chlamydia, Coxiella burnetii, Francisella tularensis, Legionella pneumophila, Listeria monocytogenes, Mycobacterium avium, Mycobacterium leprae, Mycobacterium tuberculosis Neisseria gonorrhoeae, Rickettsiae, Salmonella typhi, Shigella dysenteriae, Yersinia pestis, Plasmodium* spp, *Theileria parva, Toxoplasma gondii, Cryptosporidium parvum, Leishmania, Trypanosoma cruzi* and *Cryptococcus neoformans*.

14. The method according to claim 10, wherein the composition is substantially aqueous.

15. The method according to claim 10, wherein the mannitol is added to between 0.01% and 40% (w/v).

16. The method according to claim 15, wherein the mannitol is added to between 0.1% and 10% (w/v).

17. The method according to claim 16, wherein the mannitol is added to about 5% (w/v).

18. The method according to claim 10, wherein the stabilized composition is stored at a temperature between 10° C. and 0° C.

* * * * *